(12) United States Patent
Katakura

(10) Patent No.: US 9,757,012 B2
(45) Date of Patent: Sep. 12, 2017

(54) ENDOSCOPE WITH PLURALITY OF ILLUMINATION OPTICAL SYSTEMS

(71) Applicant: OLYMPUS CORPORATION, Hachioji-shi, Tokyo (JP)

(72) Inventor: Masahiro Katakura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/250,209

(22) Filed: Aug. 29, 2016

(65) Prior Publication Data

US 2016/0367113 A1     Dec. 22, 2016

Related U.S. Application Data

(63) Continuation of application No. PCT/JP2015/061037, filed on Apr. 8, 2015.

(30) Foreign Application Priority Data

Apr. 10, 2014    (JP) .................................. 2014-080954

(51) Int. Cl.
*A61B 1/06*          (2006.01)
*A61B 1/00*          (2006.01)
(Continued)

(52) U.S. Cl.
CPC ........ *A61B 1/00096* (2013.01); *G02B 23/243* (2013.01); *G02B 23/2469* (2013.01);
(Continued)

(58) Field of Classification Search
CPC ... A61B 1/00188; A61B 1/00163; A61B 1/06; A61B 1/07; A61B 1/00096;
(Continued)

(56) References Cited

U.S. PATENT DOCUMENTS 6,251,068 B1 *   6/2001   Akiba ................ A61B 1/00096
                                                    600/177
8,123,680 B2 *   2/2012   Kato ........................ A61B 1/05
                                                    600/129
(Continued)

FOREIGN PATENT DOCUMENTS

EP         2011428 A1    1/2009
JP         04218012 A    8/1992
(Continued)

OTHER PUBLICATIONS

Decision to Grant a Patent dated Jun. 7, 2016 issued in counterpart Japanese Application No. 2015-554379.

(Continued)

*Primary Examiner* — John P Leubecker
(74) *Attorney, Agent, or Firm* — Holtz, Holtz & Volek PC

(57) ABSTRACT

This endoscope includes an observation optical system capable of changing a magnified observation and a normal observation with each other, and a plurality of illumination optical systems, wherein a most tip side lens surface of at least one of the illumination optical systems is disposed at a position which is closer to a proximal end side than a most tip side lens surface of the observation optical system, and the following conditional expressions are satisfied.

$$0.03 < D\_Back(max)/ft < 2 \quad (1)$$
$$1.05 < ft/fw < 5 \quad (2)$$

In the expression, D_Back(max) is a maximum value of a distance between the most tip side lens surface and the most tip side lens surface, ft is a focal length in a close-distance magnified observation state, and fw is a focal length in a normal observation state.

4 Claims, 1 Drawing Sheet

(51) Int. Cl.
*G02B 23/24* (2006.01)
*A61B 1/07* (2006.01)

(52) U.S. Cl.
CPC ............ *A61B 1/00188* (2013.01); *A61B 1/06* (2013.01); *A61B 1/07* (2013.01); *G02B 23/2438* (2013.01)

(58) Field of Classification Search
CPC ............ G02B 23/2415; G02B 23/243; G02B 23/2438; G02B 6/005
USPC ........................................................ 600/177
See application file for complete search history.

(56) References Cited

U.S. PATENT DOCUMENTS

| | | | | |
|---|---|---|---|---|
| 8,545,400 | B2* | 10/2013 | Iijima | A61B 1/00096 600/164 |
| 2001/0003142 | A1* | 6/2001 | Koshikawa | A61B 1/00096 600/177 |
| 2006/0052668 | A1* | 3/2006 | Homma | A61B 1/07 600/177 |
| 2009/0048490 | A1 | 2/2009 | Iijima | |
| 2009/0156898 | A1* | 6/2009 | Ichimura | A61B 1/00089 600/127 |
| 2012/0245421 | A1* | 9/2012 | Kitano | A61B 1/00039 600/180 |
| 2013/0310649 | A1* | 11/2013 | Sone | A61B 1/00096 600/177 |
| 2015/0257630 | A1* | 9/2015 | Sone | A61B 1/00 600/109 |
| 2016/0256042 | A1* | 9/2016 | Takato | G02B 23/26 |

FOREIGN PATENT DOCUMENTS

| | | |
|---|---|---|
| JP | 09299326 A | 11/1997 |
| JP | 10239740 A | 9/1998 |
| JP | 2001346752 A | 12/2001 |
| JP | 2007289355 A | 11/2007 |
| JP | 2012125424 A | 7/2012 |
| WO | 2007122845 A1 | 11/2007 |

OTHER PUBLICATIONS

International Search Report (ISR) and Written Opinion dated Jun. 23, 2015 issued in International Application No. PCT/JP2015/061037.

Japanese Office Action dated Mar. 1, 2016 issued in counterpart Japanese Application No. 2015-554379.

* cited by examiner

ENDOSCOPE WITH PLURALITY OF ILLUMINATION OPTICAL SYSTEMS

CROSS-REFERENCE TO RELATED APPLICATIONS

This application is a Continuation application of International Application No. PCT/JP2015/061037 filed on Apr. 8, 2015, which claims priority to Japanese Application No. 2014-080954 filed on Apr. 10, 2014.

The Contents of International Application No. PCT/JP2015/061037 and Japanese application No. 2014-080954 are hereby incorporated herein by reference in its entirety.

TECHNICAL FIELD

The present invention relates to an endoscope.

BACKGROUND ART

Conventionally, there is a known endoscope whose best focus position, which can be varied within a range, is set in an area where the portions irradiated by a plurality of illumination windows, which radiate illumination light, are overlapped in order to reduce unevenness of the light intensity at the time of conducting a close-distance magnified observation by the endoscope.

CITATION LIST

Patent Literature

{PTL 1} Japanese Unexamined Patent Application, Publication No. 2001-346752

SUMMARY OF INVENTION

One aspect of the present invention is an endoscope comprising: an observation optical system capable of changing a magnified observation and a normal observation with each other by moving part of lenses in an optical axis; and a plurality of illumination optical systems which radiate illumination light to an object, wherein a most tip side lens surface of at least one of the illumination optical systems is disposed at a position which is closer to a proximal end side of the endoscope than a most tip side lens surface of the observation optical system, and the following conditional expressions are satisfied, $$0.03 < D\_Back(max)/ft < 2 \quad (1)$$

$$1.05 < ft/fw < 5 \quad (2)$$

wherein D_Back(max) is a maximum value of a distance between the most tip side lens surface of the illumination optical system and the most tip side lens surface of the observation optical system, ft is a focal length in the close-distance magnified observation state, and fw is a focal length in the normal observation state.

DESCRIPTION OF EMBODIMENTS

Embodiment

An endoscope 1 according to an embodiment of the present invention will be described below with reference to the drawings.

Figure 1:
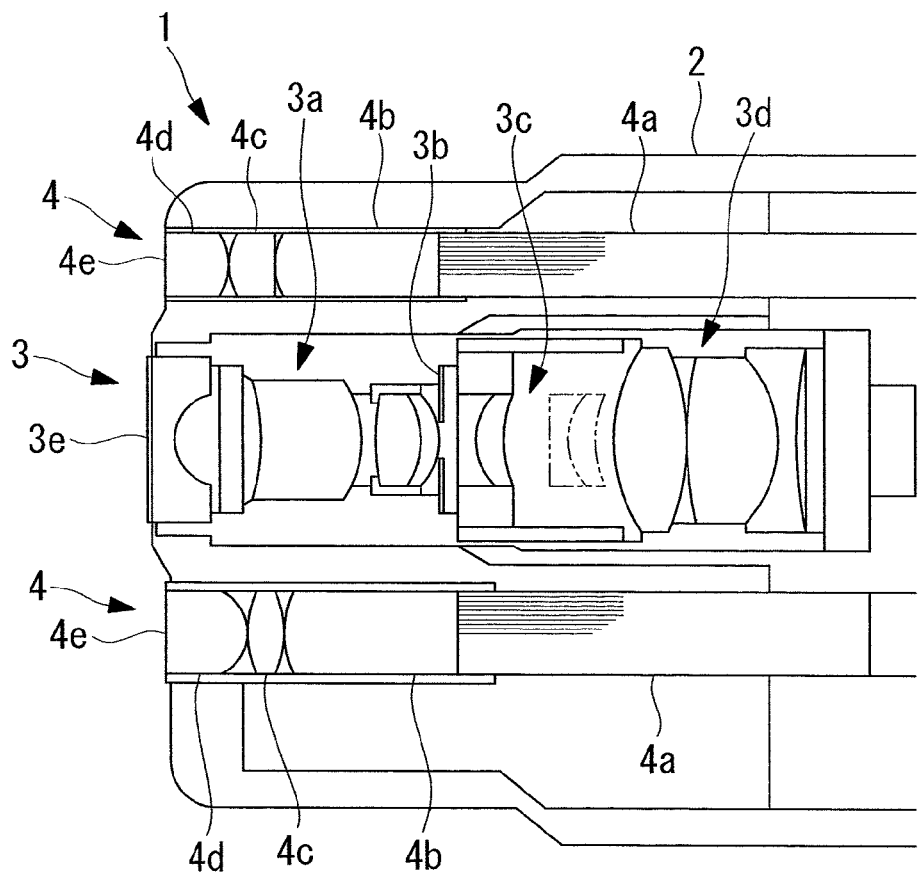
FIG. 1 is a longitudinal sectional view showing a distal end portion of an endoscope according to an embodiment of the present invention.
Figure 2:
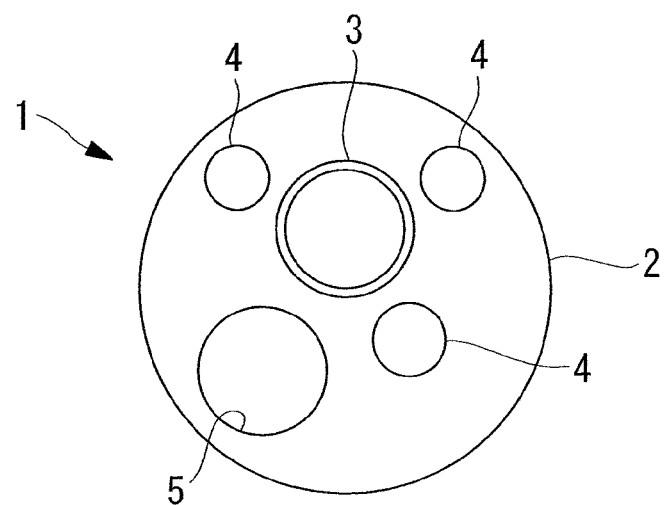
FIG. 2 is a front view of the endoscope illustrated in FIG. 1.

As shown in FIGS. 1 and 2, the endoscope 1 according to this embodiment has an observation optical system 3 and a plurality of illumination optical systems 4, and these elements are provided in a distal end portion of the inserted portion 2. In the figures, the reference symbol 5 indicates a channel for a pair of forceps.

The observation optical system 3 has a plurality of lenses arranged along an optical axis direction, and changes magnification by a structure in which part of the plurality of lenses can be moved in the optical axis direction, and thereby a magnified observation and a normal observation can be switched to each other.

More specifically, the illumination optical system 3 has, a first lens group 3a having a positive power, an aperture stop 3b, a second lens group 3c, and a third lens group 3d having a positive power, which are arranged in this order, and the illumination optical system 3 changes the magnified observation state and the normal observation state with each other by moving the second lens group 3c in the optical direction.

The illumination optical system 4 is provided at three positions around the observation optical system 3 with circumferential intervals therebetween in an example shown in FIG. 2, and has bundles of light fibers 4a, and three lenses 4b-4d disposed at the radiation ends of the bundles of light fibers 4a.

The observation optical system 3 has an optical axis which is substantially parallel to optical axes of the illumination optical systems 4, and the most tip side lens surface (first lens surface) 3e is substantially parallel to the most tip side lens surfaces (first lens surfaces) 4e.

The most tip side lens surfaces (first lens surfaces) 4e of the three illumination optical systems 4 are disposed at a position which is one level lower in the optical axis direction than the most tip side lens surface (first lens surface) 3e of the observation optical system 3. The level difference between the first lens surface 3e and the first lens surfaces 4e is called setback dimension D_Back in this embodiment.

In this embodiment, the following expressions (1)-(7) are satisfied.

$$0.03 < D\_Back(max)/ft < 2 \quad (1)$$

$$1.05 < ft/fw < 5 \quad (2)$$

$$0.01 < D\_Back(ave)/ft < 1.0 \quad (3)$$

$$0.02 < D\_Back(max)/2 \times \tan(w(t)) < 1.0 \quad (4)$$

$$-0.03 > D\_Back(max)/FL\_L01 > -1.0 \quad (5)$$

$$0.01 < D\_Back(ave)/2 \times \tan(w(t)) < 5.0 \quad (6)$$

$$-0.03 > D\_Back(ave)/FL\_L01 > -1.0 \quad (7)$$

In those expressions, D_Back(max) is the maximum value of the setback dimension, D_Back(ave) is the average value of the distances between the first lens surfaces 4e of all the illumination optical systems 4 and the first lens surface 3e of the observation optical system 3, ft is the focal length in a close-distance magnified observation state, fw is the focal length in a normal observation state, w(t) is the field of view when conducting the close-distance magnified observation, and FL_L01 is the focal length of the most tip side lens of the observation optical system 3.

In a general magnified observation endoscope, the distance between the most tip side lens surface 3e of an observation optical system 3 and the object is set to be 2-3 mm or the like, which realizes a desired observation. According to the endoscope 1 of this embodiment, since the first lens surfaces 4e of the illumination optical systems 4 are disposed at the dented position which is distant from the object relative to the first lens surface 3e of the observation optical system 3, it is possible to reduce unevenness of light distribution relative to a configuration in which the observation optical system 3 and the illumination optical systems 4 are arranged at the same level.

When the condition does not reach the lower limit of the expression (1), the setback dimension of the illumination optical systems 4 relative to the observation optical system 3 is not sufficient, and unevenness of light distribution is caused. When the condition exceeds the upper limit of the expression (1), the depth is too much and thereby part of illumination light radiated from the illumination optical systems 4 may be blocked by the observation optical system 3 and the like, which hampers desired light distribution.

Also, when the condition does not reach the lower limit of the expression (2), the magnified observation becomes difficult, the zoom ratio becomes too much, the radial dimension of the observation optical system 3 becomes large, and it becomes difficult to make the diameter of the distal end of the observation optical system 3 small, which leads reduction of insertion efficiency.

The expression (4) shows a ratio between the field of view of the observation optical system 3 and the setback dimension of the illumination optical systems 4 relative to the observation optical system 3, in a state in which the distance between the most tip side lens surface 3e of the observation optical system 3 and the object is 2 mm. When the condition does not reach the lower limit of the expression (4), the maximum value of the setback dimension is too small and thereby the light distribution cannot be improved. When the condition exceeds the upper limit of the expression (4), the field of view becomes small, and therefore it becomes unnecessary to dispose the illumination optical systems 4 at a dented position relative to the observation optical system 3.

The expression (5) shows a ratio between the focal length of the most tip side lens of the observation optical system 3 and the setback dimension of the illumination optical systems 4 relative to the observation optical system 3. When the condition does not reach the lower limit of the expression (5), the setback dimension is not sufficient and therefore light distribution is not improved, and when the condition exceeds the upper limit, the negative focal length of the most tip side lens of the observation optical system 3 is too small, and the field of view becomes too large and thereby light distribution becomes worsened.

Since the endoscope 1 is generally provided with a plurality of illumination optical systems 4, and since the light distribution of the endoscope 1 is the sum of the illumination light radiated from the plurality of illumination optical systems 4, the light distribution is largely effected not only by the maximum value of the setback dimensions of the illumination optical systems 4 relative to the observation optical system 3 but also by the average of the setback dimensions. The expressions (3), (6), and (7) are conditional expressions which are made by replacing the maximum value of the setback dimensions of the expressions (1), (4), and (5) with the average of the setback dimensions.

Since the expressions (1) and (2) are satisfied, this embodiment can afford an advantage of reducing unevenness of light distribution when conducting a close-distance magnified observation, without making the diameter of the inserted portion 2 of the endoscope 1 large. Also, since the expressions (4) and (5) are satisfied, this embodiment can afford an advantage of suppressing unevenness of light distribution even when the field of view becomes large at the time of conducting the magnified observation. Further, since the expressions (3), (6), and (7) are satisfied, this embodiment can afford an advantage of making light distribution, which is made as sum of illumination light radiated from the plurality of illumination optical systems 4, desirable at the time of conducting the magnified observation.

It is preferable that the following expressions (1')-(7') are satisfied, while the expressions (1)-(7) are satisfied in the aforementioned embodiment.

$$0.04 < D\_Back(max)/ft < 1 \tag{1'}$$

$$1.07 < ft/fw < 3 \tag{2'}$$

$$0.02 < D\_Back(ave)/ft < 0.5 \tag{3'}$$

$$0.03 < D\_Back(max)/2 \times \tan(w(t)) < 0.5 \tag{4'}$$

$$-0.04 > D\_Back(max)/FL\_L01 > -0.5 \tag{5'}$$

$$0.015 < D\_Back(ave)/2 \times \tan(w(t)) < 3.0 \tag{6'}$$

$$-0.04 > D\_Back(ave)/FL\_L01 > -0.5 \tag{7'}$$

Further, it is more preferable that the following expressions (1'')-(7'') are satisfied.

$$0.05 < D\_Back(max)/ft < 0.25 \tag{1''}$$

$$1.10 < ft/fw < 1.5 \tag{2''}$$

$$0.03 < D\_Back(ave)/ft < 0.3 \tag{3''}$$

$$0.04 < D\_Back(max)/2 \times \tan(w(t)) < 0.2 \tag{4''}$$

$$-0.05 > D\_Back(max)/FL\_L01 > -0.3 \tag{5''}$$

$$0.02 < D\_Back(ave)/2 \times \tan(w(t)) < 1.0 \tag{6''}$$

$$-0.05 > D\_Back(ave)/FL\_L01 > -0.3 \tag{7''}$$

Next, implemented examples of the endoscope 1 are described below.

The first implemented example is one whose three illumination optical systems 4 have the setback dimensions of 0.2 mm, 0.3 mm, and 0.4 mm, respectively.

The second implemented example is one whose three illumination optical systems have the setback dimensions of 0.3 mm, 0.3 mm, and 0.3 mm, respectively.

Values of the respective constants and values of the expressions (1)-(7) are shown in Table 1.

TABLE 1

| EXPRESSION | IMPLEMENTED EXAMPLE 1 | IMPLEMENTED EXAMPLE 2 |
|---|---|---|
| D_Back (max) | 0.4 | 0.3 |
| D_Back (ave) | 0.3 | 0.3 |
| ft | 1.29 | 1.63 |
| fw | 1.00 | 1.10 |

TABLE 1-continued

| EXPRESSION | IMPLEMENTED EXAMPLE 1 | IMPLEMENTED EXAMPLE 2 |
|---|---|---|
| w(t) | 40.5° | 28.6° |
| FL_L01 | −1.11 | −1.21 |
| EXPRESSION (1) | 0.310 | 0.184 |
| EXPRESSION (2) | 1.290 | 1.480 |
| EXPRESSION (3) | 0.233 | 0.184 |
| EXPRESSION (4) | 0.234 | 0.275 |
| EXPRESSION (5) | −0.361 | −0.247 |
| EXPRESSION (6) | 0.176 | 0.275 |
| EXPRESSION (7) | −0.270 | −0.247 |

According to these implemented examples, it can be seen that the expressions (1)-(7) are satisfied.

The inventor has arrived at the following aspects of the invention.

One aspect of the present invention is An endoscope comprising: an observation optical system capable of changing a magnified observation and a normal observation with each other by moving part of lenses in an optical axis; and a plurality of illumination optical systems which radiate illumination light to an object, wherein a most tip side lens surface of at least one of the illumination optical systems is disposed at a position which is closer to a proximal end side of the endoscope than a most tip side lens surface of the observation optical system, and the following conditional expressions are satisfied, $$0.03 < D\_Back(max)/ft < 2 \quad (1)$$

$$1.05 < ft/fw < 5 \quad (2)$$

wherein D_Back(max) is a maximum value of a distance between the most tip side lens surface of the illumination optical system and the most tip side lens surface of the observation optical system, ft is a focal length in a close-distance magnified observation state, and fw is a focal length in a normal observation state.

In a general magnified observation endoscope, the distance between the most tip side lens surface of an observation optical system and the object is set to be 2-3 mm or the like, which realizes a desired observation.

According to this aspect, since the most tip side lens surface of the illumination optical system is disposed at the dented position which is setback relative to the most tip side lens surface of the observation optical system, it is possible to reduce unevenness of light distribution relative to a configuration in which the observation optical system and the illumination optical systems are arranged at the same level.

The expression (1) shows that the illumination optical system is setback from the object side to the imaging element side relative to the observation optical system, and if the condition satisfies the expression (1), desired light distribution can be achieved even when conducting magnified observation. When the condition does not reach the lower limit of the expression (1), the setback dimension of the illumination optical systems relative to the observation optical system is not sufficient, and unevenness of light distribution is caused. When the condition exceeds the upper limit of the expression (1), the depth is too much and thereby part of illumination light radiated from the illumination optical systems may be blocked by the observation optical system and the like, which hampers desired light distribution.

Also, the expression (2) refers to zoom ratio of the magnified observation endoscope, when the condition does not reach the lower limit of the expression (2), the magnified observation becomes difficult, the zoom ratio becomes too much, the radial dimension of the observation optical system becomes large, and it becomes difficult to make the diameter of the distal end of the observation optical system small, which leads reduction of insertion efficiency.

In the above-described aspect, it is preferable that the following conditional expression is satisfied, $$0.01 < D\_Back(ave)/ft < 1.0 \quad (3)$$

wherein D_Back(ave) is an average value of the distances between the most tip side lens surfaces of all the illumination optical systems and the most tip side lens surface of the observation optical system.

By employing this configuration, it is possible to make light distribution, which is made as sum of illumination light radiated from the plurality of illumination optical systems, desirable at the time of conducting the magnified observation.

In the above-described aspect, it is preferable that the following conditional expressions are satisfied, $$0.02 < D\_Back(max)/2 \times \tan(w(t)) < 1.0 \quad (4)$$

$$-0.03 > D\_Back(max)/FL\_L01 > -1.0 \quad (5)$$

wherein w(t) is a field of view during the close-distance magnified observation state, and FL_L01 is a focal length of a most tip side lens of the observation optical system.

The expression (4) shows a ratio between the field of view of the observation optical system and the setback dimension of the illumination optical systems relative to the observation optical system, in a state in which the distance between the most tip side lens surface of the observation optical system and the object is 2 mm. When the condition does not reach the lower limit of the expression (4), the maximum value of the setback dimension is too small and thereby the light distribution cannot be improved. When the condition exceeds the upper limit of the expression (4), the field of view becomes small, and therefore it becomes unnecessary to dispose the illumination optical systems at a dented position relative to the observation optical system.

The expression (5) shows a ratio between the focal length of the most tip side lens of the observation optical system and the setback dimension of the illumination optical systems relative to the observation optical system. When the condition does not reach the lower limit of the expression (5), the setback dimension is not sufficient and therefore light distribution is not improved, and when the condition exceeds the upper limit, the negative focal length of the most tip side lens of the observation optical system is too small, and the field of view becomes too large and thereby light distribution becomes worsened.

In the above-described aspect, it is preferable that the following conditional expressions are satisfied.

$$0.01 < D\_Back(ave)/2 \times \tan(w(t)) < 5.0 \quad (6)$$

$$-0.03 > D\_Back(ave)/FL\_L01 > -1.0 \quad (7)$$

By employing this configuration, it is possible to make light distribution, which is made as sum of illumination light radiated from the plurality of illumination optical systems, desirable at the time of conducting the magnified observation.

In the above-described aspect, the most tip side lens surface of the observation optical system and the most tip side lens surfaces of all the illumination optical systems may be substantially parallel.

By employing this configuration, it becomes possible to achieve uniform distribution between the center of the field of view and the periphery thereof, and from the normal observation state to the magnified observation state.

The aforementioned aspects afford an advantage of reducing unevenness of light distribution and facilitating treatment even in a wide angle observation whose half angle of the field of view when conducting a close-distance magnified observation is equal to or more than 40°.

REFERENCE SIGNS LIST

1 endoscope
3 observation optical system
3$c$ lens
3$e$, 4$e$ first lens surface (the most tip side lens surface)
4 illumination optical system

The invention claimed is:

1. An endoscope comprising:
   an observation optical system capable of changing a magnified observation state and a normal observation state with each other by moving part of lenses in an optical axis; and
   a plurality of illumination optical systems which radiate illumination light to an object,
   wherein a most tip side lens surface of at least one of the illumination optical systems is disposed at a position which is closer to a proximal end side of the endoscope than a most tip side lens surface of the observation optical system, and the following conditional expressions are satisfied, $$0.03 < D\_Back(max)/ft < 2 \tag{1}$$

$$1.05 < ft/fw < 5 \tag{2}$$

wherein D_Back(max) is a maximum value [mm] of a distance between the most tip side lens surface of the illumination optical system and the most tip side lens surface of the observation optical system,
   ft is a focal length [mm] of the observation optical system in the magnified observation state,
   and fw is a focal length [mm] of the observation optical system in the normal observation state.

2. The endoscope according to claim 1, wherein the following conditional expression is satisfied, $$0.01 < D\_Back(ave)/ft < 1.0 \tag{3}$$

wherein D_Back(ave) is an average value [mm] of the distances between the most tip side lens surfaces of all the illumination optical systems and the most tip side lens surface of the observation optical system.

3. The endoscope according to claim 1, wherein the following conditional expressions are satisfied, $$0.02 < D\_Back(max)/2 \times \tan(w(t)) < 1.0 \tag{4}$$

$$-0.03 > D\_Back(max)/FL\_L01 > -1.0 \tag{5}$$

wherein w(t) is a field of view of the observation optical system during the magnified observation state, and FL_L01 is a focal length [mm] of a most tip side lens of the observation optical system.

4. The endoscope according to claim 3, wherein the following conditional expressions are satisfied, $$0.01 < D\_Back(ave)/2 \times \tan(w(t)) < 5.0 \tag{6}$$

$$-0.03 > D\_Back(ave)/FL\_L01 > -1.0 \tag{7}$$

wherein D_Back(ave) is an average value [mm] of the distances between the most tip side lens surfaces of all the illumination optical systems and the most tip side lens surface of the observation optical system.

* * * * *